United States Patent [19]

Bellmann et al.

[11] 4,332,964

[45] Jun. 1, 1982

[54] UNSATURATED ESTERS OF ADAMANTANE CONTAINING DIOLS AND THERMO-RESISTANT CROSS-LINKED POLYMERS THEREFROM

[75] Inventors: Gunter Bellmann, Onex, Switzerland; Nguyen Van Tao, Cruseilles, France

[73] Assignee: Battelle Development Corporation, Columbus, Ohio

[21] Appl. No.: 264,680

[22] Filed: May 18, 1981

Related U.S. Application Data

[63] Continuation-in-part of Ser. No. 158,504, Jun. 11, 1980.

[51] Int. Cl.³ .............................................. C07C 69/54
[52] U.S. Cl. ...................................... 560/141; 560/220
[58] Field of Search ................. 560/141, 220; 585/252

[56] References Cited

U.S. PATENT DOCUMENTS

| | | | |
|---|---|---|---|
| 3,255,268 | 6/1966 | Suld et al. | 260/666 |
| 3,342,880 | 9/1967 | Reinhardt | 260/648 |
| 3,356,751 | 12/1967 | Schneider | 585/352 |
| 3,518,241 | 6/1970 | Duling et al. | 252/89.5 |
| 3,533,947 | 10/1970 | Duling et al. | 252/57 |
| 3,580,964 | 5/1971 | Driscoll | 260/871 |
| 3,639,362 | 2/1972 | Duling et al. | 260/78.5 |
| 3,711,556 | 1/1973 | Lee | 560/141 |

FOREIGN PATENT DOCUMENTS

490795 5/1973 U.S.S.R. .............................. 560/220

*Primary Examiner*—Natalie Trousof
*Assistant Examiner*—Frederick W. Pepper
*Attorney, Agent, or Firm*—Gerald R. Black

[57] ABSTRACT

Diacrylate and dimethacrylate esters corresponding to the formula

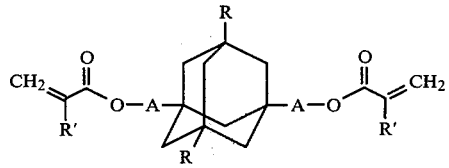

wherein R and R' are hydrogen or methyl and A is either a sigma ($\sigma$) bond; a $(CH_2)\eta$ radical where $\eta$ is an interger that may vary from one through four; or phenylene, or an alkyl derivative thereof. The new adamantane containing difunctional olefinic monomers can then be polymerized, or copolymerized with other acrylic type olefinic monomers to produce polymers with unusual physical properties, including unusual hardness, inertness to degradable agents, and resistance to heat.

8 Claims, No Drawings

UNSATURATED ESTERS OF ADAMANTANE CONTAINING DIOLS AND THERMO-RESISTANT CROSS-LINKED POLYMERS THEREFROM

This application is a continuation-in-part to the co-pending application, Ser. No. 158,504, filed on June 11, 1980, in the U.S. Patent Office.

FIELD OF INVENTION

The present invention concerns new unsaturated esters (I) of adamantane diols and of adamantane containing dihydroxy-compounds (II), the polymerization thereof and the cross-linked polymers resulting from such polymerization.

The new ester monomers have the formula (I),

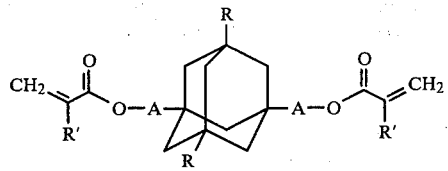

FORMULA (I)

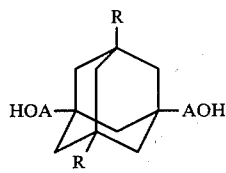

FORMULA (II)

wherein the R and R' are hydrogen or methyl group and A is either a sigma ($\sigma$) bond, a radical satisfying the formula $(CH_2)\eta$, a phenylene or an alkyl derivative thereof.

What follows is LIST I which lists some specific examples from FORMULA (I):

LIST I

1. Diacrylate and dimethacrylate esters of 1,3-adamantane diol
   R=H; R'=H, CH$_3$; A=sigma ($\sigma$) bond 2. Diacrylate and dimethacrylate esters of 1,3-dimethyl-5,7-adamantane diol
   R=CH$_3$; R'=H, CH$_3$; A=sigma ($\sigma$) bond 3. Diacrylate and dimethacrylate esters of 1,3-bis-(hydroxymethyl) adamantane
   R=H; R'=H, CH$_3$; A=—CH$_2$—

4. Diacrylate and dimethacrylate esters of 1,3-dimethyl-5,7-bis-(hydroxymethyl) admantane
   R=CH$_3$; R'=H, CH$_3$; A=—CH$_2$—

5. Diacrylate and dimethacrylate esters of 1,3-bis-(2-hydroxyethyl) admantane
   R=H; R'=H, CH$_3$; A=—CH$_2$—CH$_2$—

6. Diacrylate and dimethacrylate esters of 1,3-dimethyl-5,7-bis-(2-hydroxyethyl) adamantane
   R=CH$_3$; R'=H, CH$_3$; A=—CH$_2$—CH$_2$—

7. Diacrylate and dimethacrylate esters of 1,3-bis-(p-hydroxyphenyl) adamantane
   R=H; R'=H,CH$_3$;

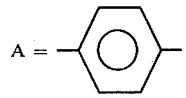

8. Diacrylate and dimethacrylate esters of 1,3-dimethyl-5,7-bis-(p-hydroxyphenyl) adamantane
   R=CH$_3$; R'=H,CH$_3$;

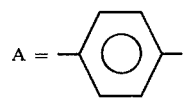

Thus, the new monomers of the invention, i.e. the acrylic and methacrylic esters of the corresponding di-hydroxy containing adamantanes (II), are difunctional compounds, a condition for obtaining, by the polymerization thereof, cross-linked type resins having unusual hardness, inertness to degradation agents and resistance to heat.

SUMMARY OF THE PRIOR ART

Esters of unsaturated acids and hydroxy-containing adamantane compounds are already known. Thus, DULING et al (U.S. Pat. Nos. 3,533,947 and 3,639,362) disclose the mono-acrylates of 1-hydroxy-adamantane and of other hydroxy-adamantanes alkylated on the other bridge-head positions of the cage. Also S. S. NOVIKOV et al., *Izvestiya Akademii Nauk SSSR*, [12] 2765, (1977), report the preparation of acrylates and methacrylates of mono substituted adamantane compounds of formula HO—R—Ad in which Ad represents the adamantane cage and R represents the groups methylene, ethylene, —CH$_2$—CH$_2$—O—CO—, —CH$_2$—CH$_2$—O—CO—CH$_2$—. Also, REINHARDT (U.S. Pat. No. 3,342,880) discloses the preparation and the polymerization of adamantyl methacrylate and of 3,3'-dimethylacryl-1,1'-bis-adamantane, the latter giving a cross-linked resin.

Now, all the monofunctional monomers of the above prior art provide straight chain polymer resins the properties of which do not come up to the level of cross-linked polymers, and the difunctional monomer mentioned above, although it provides a cross-linked polymer, is rather expensive and not well suited for industrial developments.

OBJECTS OF THE INVENTION

Thus, one object of the present invention is to provide new adamantane monomers containing two olefinic groups suitable for making, by polymerization, or copolymerization with other monomers, cross-linked resins with unusual physical properties.

Another object of the invention is to provide adamantane polymerizable difunctional monomers, the adamantane cage of which is separated from the polymerizable function by means of a connecting chain the length of which can be varied in order that polymers and copolymers with a range of properties can be obtained by using appropriate mixtures of different monomers and copolymerizing such mixtures.

Still another object of the invention is to propose new difunctional adamantane monomers which can be prepared according to well defined and relatively inexpensive routes.

Still another object of the invention is to furnish difunctional adamantane polymerizable monomers which can easily and cheaply be polymerized by different methods, i.e. thermally, by means of free radicals, or photochemically, thus ensuring a great versatility of end-uses.

Other objects of the invention will become apparent to those skilled in the art from the detailed discussion that follows:

DEFINITION OF THE INVENTION

The preferred compounds in the invention are the acrylates and methacrylates of 1,3-adamantane diol, of 1,3-bis(hydroxymethyl)-adamantane, of 1,3-bis(2-hydroxyethyl)-adamantane, of 1,3-bis(p-hydroxyphenyl)-adamantane, and also the corresponding homologs with methyl groups in position 5 and 7 of the adamantane cage. All these monomers are liquids or solids which can be polymerized easily either thermally (around 150° C.) or in the presence of radical initiators such as $H_2O_2$, or organic peroxides such as benzoyl peroxide, dicumyl peroxide, lauroyl peroxide, or azobisisobutyronitrile and other common initiators. These monomers can also be polymerized by irradiation with actinic sources such as ultraviolet light (preferably below 320 nm), and electron beam.

The monomers can be polymerized either individually or copolymerized as mixtures of two or several other monomers. Said other monomers can be selected from difunctional monomers according to the invention or from monomers of the prior art including monofunctional monomers or polyfunctional monomers. Among the monofunctional monomers, acrylic acid, acrylamide, and alkyl acrylates can be mentioned; among the polyfunctional monomers, ethylene glycol diacrylate, hexanediol diacrylate, and trimethylol propane triacrylate can be mentioned. The ratio of PTMM to the copolymers may range from 1:0 to 1:1.

The polymers of the invention are hard, transparent resins which resist attack by heat and solvents and which have many end-uses. Depending on the method of polymerization, hardnesses in the range of 30 (Knoop) and more can be attained and the weight losses on being subjected to temperatures in the range of 400°-450° C. are only about one third of the losses for cross-linked resins from conventional monomers.

Therefore, the new resins can be used in many high temperature applications and, also, for improving the scratch and solvent resistance of organic glasses by means of coatings only a few microns thick.

SOME ILLUSTRATIVE EMBODIMENTS OF THE INVENTION

The new monomers of the invention can be obtained according to several different routes some of which will be summarized in the following test by way of illustration.

Adamantane itself is available commercially and is generally obtained from the catalyzed rearrangement of tricyclic compounds. Thus, for instance, the bridgehead dimethyl hydrocarbon can be obtained from acenaphthene by hydrogenation (reaction ①) and subsequent rearrangement in the presence of Lewis acids (reaction ②).

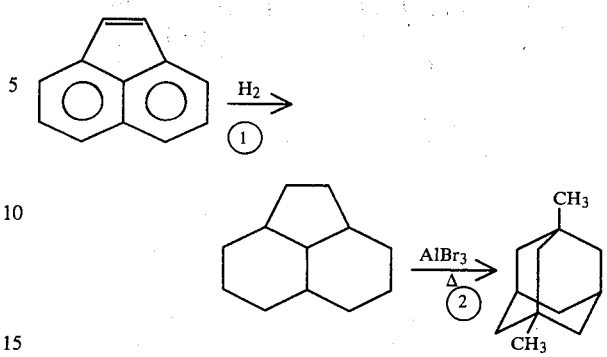

Another similar method consists in the hydrogenation of dimethyl dicylcopentadiene (reaction ①a) and the subsequent rearrangement of the hydrogenated tricyclo compound into dimethyl adamantane (reaction ②a).

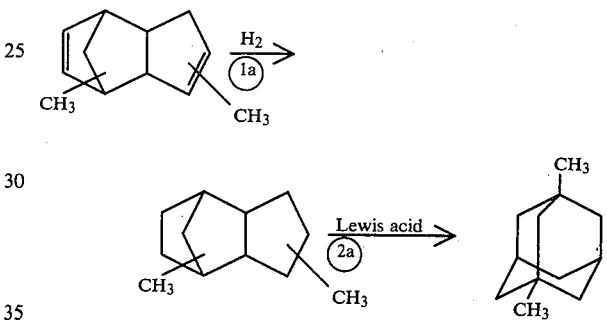

Then, dimethyl adamantane can be oxidized (reaction ③) with $CrO_3$ in acetic acid to the corresponding diol (IIa) such as described, for instance in French Pat. No. 1,461,287, or brominated to the corresponding dibromocompound (III) with bromine in the presence of boron tribromide and $AlBr_3$ (reaction ④).

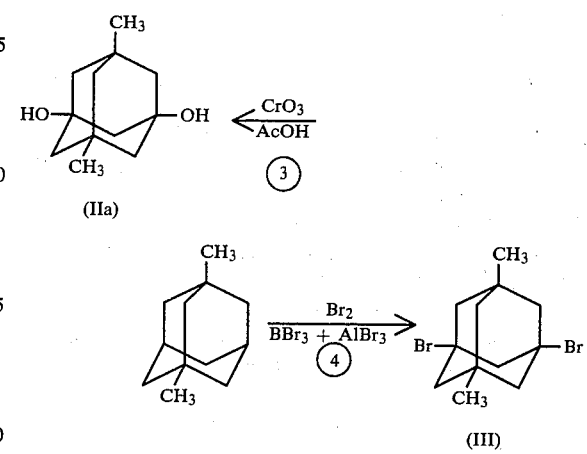

The dibromo-compound (III), as well as the diol (IIa), can be converted to the corresponding dicarboxylic acid by reaction with formic acid in concentrated $H_2SO_4$, (reaction ⑤) then the diacid is esterified with a lower alcohol (reaction ⑥) and the obtained ester is reduced to the corresponding diol (IIb) with lithium aluminum hydride (reaction ⑦).

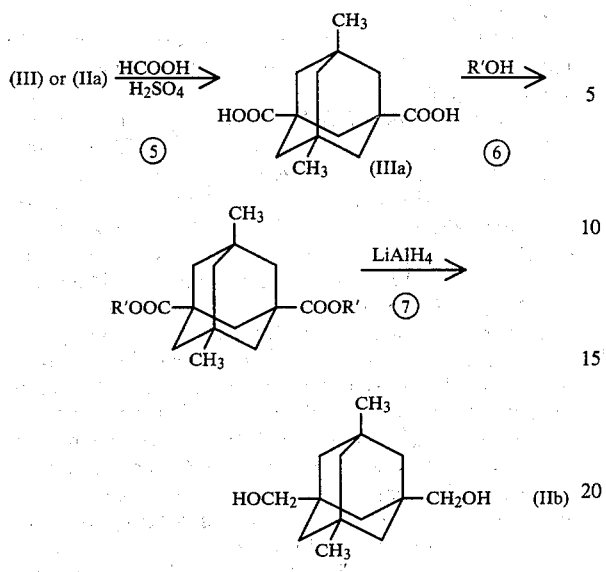

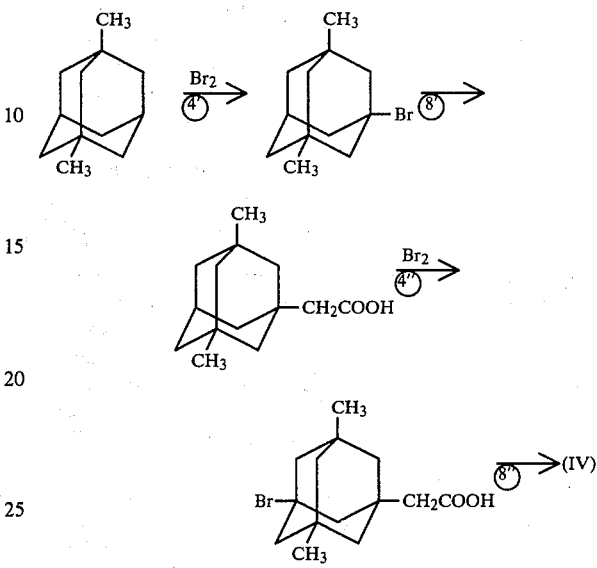

Alternatively, the dibromo-compound (III) can be converted to the corresponding diacetic acid derivative (IV), for instance by heating with vinylidene chloride in sulfuric acid (reaction ⑧), according to K. BOTT, Chem. Ber. 101, 564–573 (1968). The diacid being thereafter esterified and the ester reduced with LiAlH$_4$ in a manner analogous to reactions ⑥ and ⑦ above (reactions ⑥' and ⑦') to give the diethylol compound (IIc).

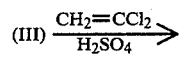

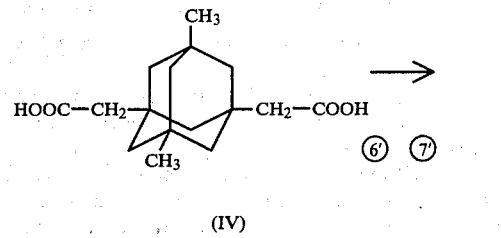

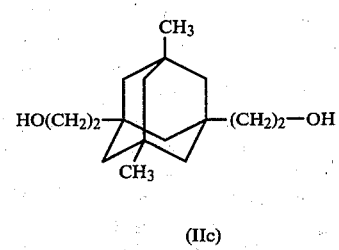

However, since the sequence of reactions ⑧, ⑥' and ⑦' does not provide very good yields, a two stage analogous sequence of reactions involving the corresponding monobromo-adamantane derivative is preferably used. In this sequence, dimethyl adamantane is first monobrominated using refluxing bromine (reaction ④) and the dimethyl-bromo-adamantane is converted to the mono-methyl-carboxylic acid by the same type of reaction as reaction ⑧ above, after which the monocarboxylic compound is brominated yielding 1-bromo-3-carboxymethyl-5,7-dimethyl adamantane which then is once more reacted with vinylidene chloride in H$_2$SO$_4$ according to ⑧ to give, finally, the diacetic acid (IV):

The dibromo-dimethyl-adamantane (III) can also be reacted with phenols according to the conditions disclosed in U.S. Pat. No. 3,594,427 (reaction ⑨) to give the desired bishydroxyphenyl compounds (IId). This is illustrated by the following scheme involving ordinary unsubstituted phenol:

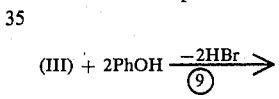

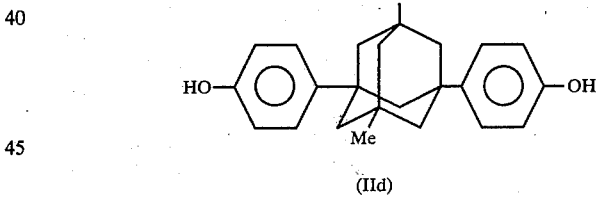

It should be pointed out that the same reactions can be used for obtaining the corresponding non-methylated adamantane bishydroxy-compounds.

Now, the compounds of formula (II) can be converted to the monomers (I) by esterification, preferably with acrylyl chloride or methacrylyl chloride in the presence of a tertiary amine, according to well known techniques (see for examples U.S. Pat. No. 3,533,947). The reaction is carried out by dissolving the alcohol in a solvent such as benzene, toluene, tetrahydrofuran or the like, adding a tertiary amine to the mixture in molar excess relative to the alcohol, and then slowly adding the acid chloride thereto. The amine used preferably is triethylamine, although other tertiary amines such as pyridine, tributylamine, N,N,N',N'-tetramethylethylenediamine, triethylenediamine, picolines, quinoline and the like can be employed. Upon addition of the acid chloride, the initial reaction that takes place involves the formation of a complex between it and the amine. Slow addition of the acid chloride is continued preferably until the amount added is in molar excess of the alcohol. The resulting slurry is then stirred at a temperature in the range of 10°–80° C., preferably 20°–60° C., to effect the esterification reaction. A temperature above 80° C. should be avoided in most instances as this tends to cause a messy reaction, and it is most preferable to maintain the temperature in the range of 25°–60° C. Time required for completion of the reaction will depend upon the reaction temperature used, but generally is in the range of one to twenty hours.

As the reaction occurs the amine-acid chloride complex is replaced by an amine HCl complex which is insoluble in the solvent. The alkyl adamantyl-acrylate product on the other hand remains in solution. After completion of the reacton, the mixture is filtered to remove the amine-HCl complex and the solvent is removed by evaporation. The crude product ester obtained is a nearly colorless liquid or solid which can be purified by liquid partition chromatography, by column chromatography (on $Al_2O_3$) or, when crystallization occurs, by recrystallization in a suitable solvent. The purified products are colorless liquids or solids. In the absence of suitable stabilizing additives, the liquids may, in some cases, polymerize spontaneously on storage but this generally occurs slowly enough to allow end use application beforehand.

For polymerizing the monomers of the invention, conventional techniques can be used. For instance, the monomers can be heated, either pure or in admixture with other monomers, at temperatures where polymerization will occur thermally. Temperatures in the range of 150° C. and over are ordinarily suitable.

Otherwise, free radical promoters or irradiation in the presence of photoinitiators can be used when polymerization is to be carried out at lower temperature, e.g. room temperature. Conditions for photopolymerization are also conventional and can be found in the following reference: *UV Curing Science and Technology*, Editor: Technology Marketing Corp. (1978) Stamford, Conn.

For instance, a coating of protective polymer according to the invention can be applied on organic glasses made, for example, of transparent resins such as polycarbonate or polymethacrylate. For this, the monomers of the invention (either pure or in admixture with other monomers) and a photoinitiator are applied as a thin layer over the surface of said organic glass and the whole is subjected to irradiation for periods ranging from a few seconds to several minutes by means of ultraviolet radiation, e.g. a high pressure mercury lamp, the emission of which is mainly in the ultraviolet wavelengths (300–330 nm) or the short visible wavelengths. The pieces of organic glasses thus acquire a very hard, solvent-resistant and transparent protective film enabling them to be used in applications where resistance to solvents, especially chlorinated solvents, and mechanical abuse is a problem, e.g. transparent construction plates, optical material, etc.

The examples below further illustrate the invention in more detail.

EXPERIMENTAL

Example 1

Preparation of the diacrylate ester of 1,3-dimethyl-5,7-adamantane-diol (Compound (I), R=CH₃; R'=H)

(a) Oxidation of 1,3-dimethyladamantane with chromic anhydride:

This reaction was carried out as described in French Pat. No. 1,461,287 and gave the corresponding diol in yields of about 85%.

(b) Esterification of diol (IIa) with acrylyl chloride 9.55 g (48.6 mmole) of 1,3-dimethyl-5,7-adamantanediol was dissolved in a solution of 14 ml (100 mmole) of triethylamine in 400 ml of anhydrous tetrahydrofuran (THF) at 40° C. The solution was kept between 40° and 50° C. while adding, dropwise with stirring, 8.1 ml (100 mmole) of acrylyl chloride. The addition lasted 45 minutes. Stirring was continued for one hour afterwards and the insoluble triethylamine hydrochloride was removed by filtration. The solid was dried and weighed, the result corresponding practically to the expected theoretical weight and showing that the reaction is about quantitative. The filtrate was concentrated under reduced pressure (12 Torr; 50° C.) until 14.8 g of the crude diacrylate was obtained. The crude product was easily purified by column chromatography on $Al_2O_3$ using hexane or chloroform as eluent. MP of the pure diacrylate was 45.5°–46° C. The NMR spectrum was taken in $CDCl_3$ using TMS as the internal standard. The chemical shifts are given in ppm (δ).

1.00 (s,6H):

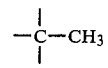

; 1.20 (s,2H): adamantane-$CH_2$—; 1.86 (s,8H): adamantane-$CH_2$—; 2.48 (s,2H): adamantane-$CH_2$—; 5.65 (m complex), 6H): —CO—CH=$CH_2$.

EXAMPLE 2

Preparation of diacrylate and dimethacrylate ester of 1,3-dimethyl-5,7-bis-(2-hydroxymethyl)adamantane (a) Dibromination of dimethyladamantane (reaction ④).

This dibromination to 1,3-dimethyl-5,7-dibromoadamantane can be carried out according to known techniques using bromine in the presence of Lewis acids such as $AlBr_3$ and $BBr_3$. The present preparation was performed according to E. R. TALATY et al., *J. Chem, Soc.* (C) 1968, 1902. Thus, 328 g of dimethyladamantane (2 mole) was treated with 1.04 l of anhydrous bromine in the presence of 50 ml $BBr_3$ and 2.2 g of $AlBr_3$ to give 510 g of the desired product (80% yield).

(b) Conversion of the dibromo-dimethyl-adamantane (III) or the corresponding dihydroxy-compound (IIa) to the corresponding dicarbodylic acid (IIIa)

This reaction was carried out according to the directions given in French Pat. No. 1,476,992. Thus, treating 165 g (0.51 mole) of 1,3-dimethyl-5,7-dibromoadamantane in 1.8 l of sulfuric acid (103% $H_2SO_4$ equiv.) with 190 ml of HCOOH at 10° C. gave, after hydrolysis, 121.3 g of the desired dicarboxylic acid (yield 94%).

Similar results were obtained when using, as the starting material, the corresponding 1,3-dimethyl-5,7-adamantane-diol.

(c) Esterification of the dimethyl-adamantane-dicarboxylic acid (IIIa)

Esterification of the above compound can be performed according to conventional techniques, e.g. by the direct interaction with a lower alcohol such as MeOH, EtOH in the presence of catalysts such as $H_2SO_4$, $BF_3$, tosylic acid and the like. Another route is the conversion of the diacid into its dichloride followed by reaction of the latter with the lower alcohols. Thus, 31 g (0.12 mole) of 1,3-dimethyladamantane-5,7-dicarboxylic acid was boiled for four hours under reflux with 160 ml $SOCl_2$. The excess of thionyl chloride was removed under reduced pressure and the residue was dissolved into 100 ml $CCl_4$ to which was added an excess of absolute ethanol. The solvent and excess alcohol were stripped off and the crude diester was distilled under reduced pressure (B.P./0.8 Torr: 135°–139° C.); yield 34.9 g (92%) NMR spectrum ($CCl_4$; TMS; ppm $\delta$).

0.92 (s,6H): —C—$CH_3$; 1.17 (s,2H): adamantane-$CH_2$—;
1.23 (t,6H, J=7.2 cps): —$CH_3$ (of ethoxy);
1.48 (s,8H) adamantane-$CH_2$;
1.82 (s,2H): adamantane-$CH_2$;
4.10 (g,4H, J=7.2 cps): —$CH_2$— (of ethoxy).

(d) Reduction of the dimethyl-adamantane dicarboxylate with $LiAlH_4$ (reaction ⑦).

Six grams of lithium-aluminum hydride (0.158 mole) was stirred with 200 ml of absolute ether and to this was added dropwise 24.15 g (0.078 mole) of diethyl 1,3-dimethyladamantane-5,7-dicarboxylate in 50 ml of absolute ether at a rate such as to maintain gentle refluxing of the solvent. Refluxing was continued for two hours. Then the excess $LiAlH_4$ was decomposed with moist AcOEt. The reaction mixture was acidified with 20% $H_2SO_4$ which gave, by crystallization, 15.3 g of 1,3-dimethyl-5,7-bis (hydroxymethyl)-adamantane (IIb) which was collected by filtration. Another 1.8 g crop was obtained from the filtrate after separating the water phase and evaporating the organic layer. Yield was 17.1 g (97%). MP was 158°–161° C. Recrystallization from ethyl acetate afforded a product MP 160°–162° C.

NMR spectrum (DMSO-$d_6$+$CDCl_3$, TMS, ppm $\delta$).
0.87 (s,6H):

$$-\underset{|}{\overset{|}{C}}-CH_3;$$

1.10 (s,12H): adamantane-$CH_2$—;
3.16 (d,4H, J=6 cps): —$CH_2$—OH;
3.93 (t,2H, J=6 cps): —$CH_2$—OH.

(e) Esterification of the 1,3-dimethyl-5,7-bis (hydroxymethyl)-adamantane (IIb) into the corresponding diacrylic and dimethacrylic esters (I), R=$CH_3$; R'=H, $CH_3$; A=—$CH_2$—.
1. Reaction with acrylyl chloride.

To a solution of 11.15 g of 1,3-dimethyl-5,7-bis (hydroxymethyl)-adamantane (49.7 mmole) in 280 ml of benzene and 16.7 ml (120 mmole) of triethylamine was added, dropwise at room temperature, 8.84 ml (109 mmole) of acrylyl chloride over a 45 minute period. The temperature rose to about 40° C. and triethylamine hydrochloride separated. The suspension was further stirred for one hour at 40° C. after which it was filtered and the solid was washed with benzene. The combined washings and filtrate was extracted with, successively, water, saturated aqueous $NaHCO_3$, 5% HCl and finally water. The benzene solution was dried on anhydrous $Na_2SO_4$ and concentrated below 40° C., leaving a viscous colorless residue that crystallized on standing in the cold. Yield 13.2 g (80%) of diacrylate (I), R=$CH_3$; R'=H; A=—$CH_2$—. The product was crystallized from EtOH—$H_2O$ giving colorless crystals having a MP 49°–50.5° C.

NMR spectrum ($CCl_4$, TMS, ppm $\delta$)
0.87 (s,6H):

$$-\underset{|}{\overset{|}{C}}-CH_3;$$

1.16 (s,12H): adamantane—$CH_2$—;
3.80 (s,4H): —$CH_2$O—;
5.6–6.7 (complex m,6H): —CO—CH=$CH_2$ 2. Reaction with methacrylyl-chloride Methacryl chloride (12.3 ml, 127.3 mmole) was added dropwise at 40° C. to a solution of 12.97 g (57.8 mmole) of 1,3-dimethyl-5,7-bis(hydroxymethyl)adamantane in 315 ml of dry benzene containing 17.7 ml (127.3 mmole) of $Et_3N$. After the addition was complete, stirring was continued for five hours at 60° C. and, thereafter, the precipitated hydrochloride was filtered off and washed with benzene. The combined filtrate and washings were scrubbed as described above in the case of the diacrylate and, after drying the organic phase and evaporating the solvent, 18.7 g (90%) of the dimethycrylate (I), R=R'=$CH_3$; A=—$CH_2$—, was recovered as a viscous residue. This was further purified by column chromatography on $Al_2O_3$ using $CHCl_3$ as eluent. Analysis showed that it was reasonably pure but it did not crystallize.

NMR spectrum ($CDCl_3$, TMS, ppm $\delta$)
0.87 (s,6H):

$$-\underset{|}{\overset{|}{C}}-CH_3;$$

1.18 (s,12H): adamantane—$CH_2$—;
1.97 (d,6H, J=~1 cps): —$CH_3$ (of the methacryl group)
3.85 (s,4H): —$CH_2$—O—;

5.61 (m,2H)
6.16 (m,2H)  } $\overset{H}{\underset{H}{>}}C=C\overset{}{\underset{}{<}}$

EXAMPLE 3

Preparation of diacrylate and dimethacrylate esters of 1,3-dimethyl-5,7-bis(2-hydroxyethyl)adamantane (I), R=$CH_3$; R'=H, $CH_3$; A=—$CH_2$—$CH_2$—

(a) 1,3-dimethyl-5,7-adamantanediacetic-acid diethylester 1,3-dimethyl-5,7-adamantanediacetic acid (IV) was prepared by known techniques [K. BOTT, Chem. Ber., 101 564 (1968)]. Esterification can be achieved by the same conventional techniques mentioned under Example 2C. Thus, 28.7 g of 1,3-dimethyl-5,7-adamantane diacetic acid (0.10 mole) was boiled with an excess of absolute ethanol and 1.2 ml concentrated sulfuric acid for twelve hours under reflux to yield 31.7 g of diethyl ester (91%) BP 0.45 Torr 140°–145° C.

NMR SPECTRUM ($CCl_4$ solution, TMS as internal standard, ppm ($\delta$)
0.85 (s,6H): —C—$CH_3$ 1.20 (s,12H): adamantane—CH$_2$—
1.20 (t,6H, J=7 cps): —O—CH$_2$—CH$_3$
2.05 (s,4H):

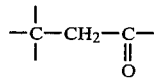

4.05 (q,4H, J=7 cps): —O—CH$_2$—CH$_3$ (b) 1,3-dimethyl-5,7-bis(2-hydroxyethyl)adamantane (IIc)

The diol (IIc) was obtained by reducing the 1,3-dimethyl-5,7-adamantanediacetic acid diethylester with lithium aluminum hydride: To 7.5 g LiAlH$_4$ (197.6 mmole) in 250 ml dry ether was added 30.2 g of diester (89.8 mmole) dissolved in 50 ml ether at such a rate that a gentle refluxing of the solvent is maintained. Refluxing was continued for an additional two hours after which time the excess LiAlH$_4$ was decomposed with ethyl acetate and water. The reaction mixture was acidified with H$_2$SO$_4$ 20% and filtered, leaving 6.15 g of diol (IIc). A further 13.3 g of diol was obtained from the filtrate after separating and evaporating the organic layer. Yield 19.45 g (86%) of diol (IIc). MP: 133°–135° C. (from ether).

NMR Spectrum (DMSO-d$_6$ solution, TMS as internal standard, ppm ($\delta$)
0.77 (s,6H):

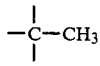

1.04 (s,12H): adamantane—CH$_2$—
1.27 (t,4H, J=7.5 cps): —CH$_2$—CH$_2$—O—
3.43 (t,4H, J=7.5 cps): —CH$_2$—CH$_2$—O—

(c) Esterification of 1,3-dimethyl-5,7-bis(2-hydroxyethyl) adamantane into the corresponding diacrylic and dimethacrylic esters (I), R=CH$_3$, R'=H, CH$_3$; A=—CH$_2$—CH$_2$—

1. Reaction with acrylyl chloride

To 5 g of 1,3-dimethyl-5,7-bis-(2-hydroxyethyl) adamantane (19.8 mmole) in 120 ml dry tetrahydrofuran (THF) containing 6.08 ml triethylamine (43.6 mmole) was added 3.52 ml acrylyl chloride (43.6 mmole) during a 25 minute period, while maintaining the temperature at 45°–50° C. Stirring was continued for five hours at 60° C. The precipitated triethylamine hydrochloride was filtered off and washed with THF. The filtrate and washings were evaporated to dryness and the residue redissolved in benzene. The benzene was successively extracted with water, saturated bicarbonate solution and water and finally dried. Evaporation of the solvent provided 6.7 g (94%) of diacrylate (I), R=CH$_3$; R'=H; A=—CH$_2$—CH$_2$—. Further purification was achieved by column chromatography on Al$_2$O$_3$ using chloroform as the eluent.

NMR Spectrum (CCl$_4$, TMS as internal standard, ppm ($\delta$)
0.82 (s,6H):

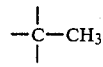

1.11 (s,12H): adamantane—CH$_2$—
1.45 (t,4H, J=7.5 cps): —CH$_2$—CH$_2$—O—
4.15 (t,4H, J=7.5 cps): —CH$_2$—CH$_2$—O—
5.6–6.6 (complex m,6H):

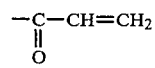

2. Reaction with methacrylyl chloride

The same condition as for the reaction with acrylyl chloride were found suitable, except for using instead 4.2 ml methacrylyl chloride (43.6 mmole). The yield was 7.3 g (95%) of dimethacrylate (I), R=R'=CH$_3$, A=—CH$_2$—CH$_2$—. Further purification was achieved by column chromatography on Al$_2$O$_3$ using chloroform as the eluent.

NMR Spectrum (CCl$_4$ solution, TMS as internal standard, ppm ($\delta$)
0.83 (s,6H): —C—CH$_3$
1.13 (s,12H): adamantane—CH$_2$—
1.48 (t,4H, J=7.5 cps): —CH$_2$—CH$_2$—O—
1.92 (d,6H, J=1 cps):

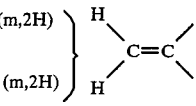

4.12 (t,4H, J=7.5 cps): —CH$_2$—CH$_2$—O—

EXAMPLE 4

Preparation of diacrylate and dimethacrylate esters of 1,3-bis-(2hydroxyethyl)adamantane (I), R=H; R'=H, CH$_3$; A=—CH$_2$—CH$_2$—

(a) 1,3-adamantane-diacetic acid diethylester

Esterification of commercially available 1,3-adamantane diacetic acid (Aldrich Chemical Co., Inc.) can be achieved by conventional techniques as mentioned heretofore. In this case, the acid chloride method was used. Thus, 20.8 g of 1,3-adamantane-diacetic acid (82.4 mmole) was boiled with 100 ml thionylchloride under reflux for four hours. The excess thionylchloride was then evaporated off and the resulting crude acid chloride was dissolved in 65 ml carbon tetrachloride and subsequently treated with an excess absolute ethanol. The solvent and excess alcohol were stripped off and the crude diester was distilled under vacuum.

BP 0.1 Torr=149°–150° C. Yield 22.6 g (89%).

NMR Spectrum (CCl$_4$ solution, TMS as internal standard, ppm ($\delta$)
1.17 (t,6H, J=7 cps): —O—CH$_2$—CH$_3$
1.33–1.63: (complex m,12H) adamantane—CH$_2$—
1.97 (s,4H):

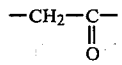

2 (m,2H):

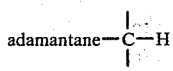

4.05 (q,4H, J=7 cps): —O—CH$_2$—CH$_3$ (b) 1,3-bis-(2-hydroxyethyl)adamantane

This diol can be obtained by reducing the 1,3-adamantane-diacetic acid diethylester with lithium aluminium hydride:

To 5.65 g LiAlH$_4$ (148.9 mmole) in 185 ml dry ether was added 22.5 g of the diester (73 mmole) in 40 ml ether at such a rate as to maintain the solvent under gentle reflux. Refluxing was continued for a further 2.5 hours and, thereafter, the excess LiAlH$_4$ was decomposed with ethylacetate and water. The reaction mixture was acidified with 20% H$_2$SO$_4$ and the organic layer was separated and washed to neutrality with water. Crystals of the pure diol then separated. Yield 12.6 g (77%).

NMR Spectrum (DMSO-d$_6$ solution, TMS as internal standard, ppm (δ)

1.03–1.7 { (complex m, 12H): adamantane—CH$_2$—

(t,4H, J = 7.5 cps): —CH$_2$—CH$_2$—OH 1.95 (m,2H): adamantane—C—H
3.48 (t,4H), J=7.5 cps): —CH$_2$—CH$_2$—OH
4.08 (s,2H)

(c) Esterification of 1,3-bis(2-hydroxyethyl) adamantane to give the corresponding diacrylic and dimethacrylic esters (I), R=H, R'=H,CH$_3$; A=—CH$_2$—CH$_2$—

1. Reaction with acrylyl chloride

To 5 g (22.3 mmoles) of 1,3-bis(2-hydroxyethyl) adamantane in 120 ml of dry benzene containing 6.83 ml of triethylamine (49.1 mmoles) was added, at 45° C., 3.97 ml acrylyl chloride (49.1 mmoles). Stirring was continued for five hours at 60° C., and the precipitated triethylamine hydrochloride was filtered off and washed with benzene. The combined filtrate and washings were extracted with water, saturated bicarbonate solution and water and finally dried. Evaporation of the solvent yielded 7.0 g (95%) of diacrylate (I), R=R'=H; A=—CH$_2$—CH$_2$—. Further purification was achieved by column chromatography on Al$_2$O$_3$ using chloroform as the eluent.

NMR Spectrum (CCl$_4$ solution, TMS as internal standard, ppm (δ).

1.17–1.83 { (complex m, 12H): adamantane—CH$_2$—

(t,4H, J = 7.5 cps): —CH$_2$—CH$_2$—O—

2.05 (m,2H):

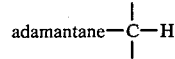

4.22 (t,4H, J=7.5 ps): —CH$_2$—CH$_2$—O—
5.6–6.6 (complex m, 6H): —CO—CH=CH$_2$

2. Reaction with methacryl chloride

The same conditions were used as with the previous case but 4.74 ml (49.1 mmoles) of methacrylyl chloride was used instead of the acrylyl chloride. The yield was 7.78 g (97%) of dimethacrylate (I), R=H; R'=CH$_3$; A=—CH$_2$—CH$_2$—. Further purification was carried out by column chromatography (Al$_2$O$_3$; CHCl$_3$).

NMR Spectrum (CDCl$_3$, TMS as internal standard, ppm (δ).

1.17–1.80 { (Complex m, 12H): adamantane—CH$_2$—

(t,4H, J = 7.5 cps): —CH$_2$—CH$_2$—O—

1.96 (d,6H, J=1 cps):

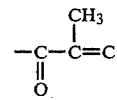

~2. (m,2H):

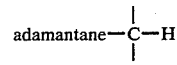

4.23 (t,4H, J=7.5 cps): —CH$_2$—CH$_2$—O—

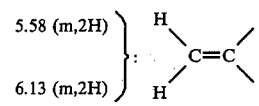

EXAMPLE 5

Preparation of diacrylate and dimethacrylate esters of 1,3-dimethyl-5,7-bis(p-hydroxyphenyl)adamantane (I), R=CH$_3$; R'=H,CH$_3$;

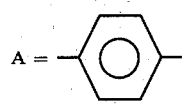

(a) 1,3-dimethyl-5,7-bis(p-hydroxyphenyl)adamantane (IId)

Adamantane bisphenols can be readily made available from the corresponding dibromoderivatives and phenol according to U.S. Pat. No. 3,594,427. Thus, 112 g of 1,3-dimethyl-5,7-dibromoadamantane (III) (0.35 m) (see Example 2a) and 900 g of phenol were heated together at 170° C. for six hours. After termination of the evolution of HBr, the mixture was heated to 220° C. for a further two hour period and the excess phenol was distilled off. The reaction mixture was poured into warm water and the white precipitate was filtered, washed with warm water and dried at 80° C. under vacuum. Yield 117.8 g (97%). The product was recrystallyzed from toluene. MP: 222°–224° C.

(b) Esterification of the 1,3-dimethyl-5,7-bis(p-hydroxyphenyl)adamantane into the corresponding diacrylic and dimethacrylic esters (I), R=CH₃; R=H, CH₃;

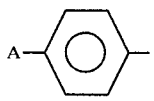

1. Reaction with acrylyl chloride

To 5 g of 1,3-dimethyl-5,7-bis(p-hydroxyphenyl)adamantane (14.3 mmoles) in 120 ml dry tetrahydrofuran containing 4.4 ml triethylamine (31.6 mmoles) was added 2.55 ml acrylyl chloride (31.6 mmoles) during 25 minutes, while maintaining a reaction temperature of 45°–50° C. Stirring was continued for four hours at 60° C. and the solvent was evaporated under vacuum. The crude reaction product (7 g) was crystallyzed from ethyl acetate. The yield was 5.2 g (80%) of pure diacrylate (I), R=CH₃; R'=H; A=p-Ph; MP: 145°–147° C.

NMR Spectrum 0.95 (s,6H):

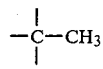

1.23 (s,2H): adamantane—CH₂—
1.55 (s,8H): adamantane—CH₂—
1.85 (s,2H): adamantane—CH₂—
5.8–6.8 (complex m,6H):

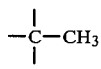

7.05 (d,4H, J = 9 cps)  
7.42 (d,4H, J = 9 cps)  } : aromatic C—H

2. Reaction with methacrylyl chloride

This was performed as above but using, instead of the acrylyl chloride, 3.04 ml of methacrylyl chloride (31.6 mmole). The yield of dimethacrylate (I), R=R'=CH₃;

A = 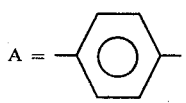

was 5.6 g (81%) MP: 159.5°–161° C. (from ethyl acetate).

NMR Spectrum 0.95 (s,6H):

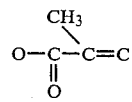

1.23 (s,2H): adamantane—CH₂—
1.57 (s,8H): adamantane—CH₂—
1.87 (s,2H): adamantane—CH₂—
2.03 (d,6H, J=1 cps)

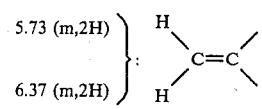

5.73 (m,2H)  
6.37 (m,2H)  } : 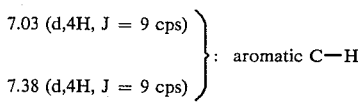

7.03 (d,4H, J = 9 cps)  
7.38 (d,4H, J = 9 cps)  } : aromatic C—H

While p-phenylene was used in this example, it is expected that alkyl derivatives of phenylene could also be so utilized.

EXAMPLE 6

Thermal and free radical polymerization of some monomers of LIST I (a) Thermal polymerization of the diacrylates.

The diacrylates (I) were subjected to heating neat at temperature ranging from 150°–200° C. until they had completely hardened. Required heating times were extremely variable, ranging from several minutes to several hours.

The compounds, identified by their substituents, the polymerization conditions and the results on hardness are summarized in Table 1 below.

TABLE 1

| Thermal polymerization of adamantane diacrylates (I) | | | | | |
|---|---|---|---|---|---|
| R | R' | A | T. °C. | reaction time hr. | Hardness (Knoop) |
| CH₃ | H | —CH₂— | 150 | 1 | — |
| CH₃ | H | —CH₂— | 200 | 0.1 | 18.33 |
| H | H | —CH₂—CH₂ | 200 | 0.1 | 17.49 |
| CH₃ | H | 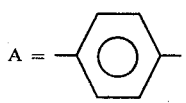 | 150 | 12 | — |

(b) Free radical catalyzed polymerization of the diacrylates and dimethacrylates.

The diacrylates and dimethacrylates (I) were free radical polymerized using small amounts of standard initiator catalysts and temperatures of 20° to 150° C. depending on the kind of initiator. In this manner, very hard, colorless, transparent, highly cross-linked resins were obtained which were infusible and found insoluble in all solvents tried. The solvents tried were 1,1,1-trichloroethane; chloroform; 1,2-dichloroethane; benzene; toluene; xylene; acetone; methyl ethyl ketone; and butyl acetate. Examples are summarized below using lauroyl peroxide as the initiator. Compounds (I) are identified by their substituents R and R'.

TABLE 2

Free radical polymerization of adamantane diacrylates and dimethacrylates (I)

| R | R' | A | Initiator (percent) | T. °C. | reaction time hr. | Hardness (Knoop) |
|---|---|---|---|---|---|---|
| CH₃ | H | —CH₂ | (0.5) | 80 | 4 | 22.29 |
| CH₃ | CH₃ | —CH₂ | (0.5) | 90 | 4 | 29.80 |
| H | CH₃ | —CH₂—CH₂ | (0.5) | 90 | 12 | 25.84 | photopolymerized in the presence of 1% of benzophenone as films about 5.8 microns thick deposited on substrates of either aluminum, polyester (MYLAR), polymethacrylate (LUCITE) or polycarbonate (MACROLON) and placed for one minute at 25 cm from a PHILIPS HOK 1 KW ultraviolet lamp, at the temperatures indicated in the table. Mixtures of monomers (I) and conventional monomers as well as controls obtained from conventional monomers and two of the bare substrate are also included in the table.

TABLE 3

| Monomer (I) | | | Other monomer (M) | | Pol. temp. | Hardness | % weight loss at 450° C. | Temperature of highest decomposition | Resistance to |
| R' | R | A | (weight ratio(I)/(M)) | Substrate | (°C.) | (Knoop) | (heating rate 6° C./min in air) | rate | CHCl₃ |
|---|---|---|---|---|---|---|---|---|---|
| H | CH₃ | — | — | all | 50 | — | — | — | good |
| H | CH₃ | CH₂ | — | all | 50 | — | 27.1 | 480 | good |
| H | H | C₂H₄ | — | all | 20 | — | 64.7 | 420 | good |
| H | CH₃ | ⌬ | — | all | 150 | — | 24.9 | 550 | excellent |
| CH₃ | CH₃ | ⌬ | — | all | 150 | — | 29.6 | 540 | excellent |
| CH₃ | CH₃ | CH₂ | — | all | 20 | 28 | — | — | good |
| CH₃ | CH₃ | C₂H₄ | — | all | 20 | 21 | — | — | good |
| H | CH₃ | CH₂ | acrylic acid (2/1) | all | 20 | — | 27.3 | 470 | good |
| — | — | — | Hexane diol diacrylate (HDD) | all | 20 | — | 77.8 | 420 | poor |
| — | — | — | HDD + acrylic acid (2/1) | all | 20 | — | 74.9 | 430 | poor |
| — | — | — | none | MAKROLON (M) | — | 13 | — | — | no resistance |
| — | — | — | none | Plexiglass | — | 22 | — | — | no resistance |

EXAMPLE 7

Photopolymerization of some monomers of LIST I

The monomers of formula (I) in liquid form, either neat (melted) or dissolved in other liquid olefinic compounds (e.g. acrylic acid, acrylates or acrylamides) were mixed with small amounts of standard photoinitiators (e.g. aromatic ketones) and spread with conventional means (including a doktor knife, painting, spraying and dipping) as thin layers (e.g. 1 to 50μ but preferably in the range of from 2 to 20μ) over transparent plates of organic glasses (e.g. polymethacrylates (LUCITE) or polycarbonates (MAKROLON, Bayer)). Then, the coated plates were photopolymerized at various temperatures for periods ranging from a few seconds to about a minute using an ultraviolet light source. The organic glasses thus coated were totally inert when immersed into chlorinated solvents (e.g. CHCl₃, trichlorethylene o-dichlorobenzene, etc.) whereas non-coated controls will either swell or dissolve under the same conditions. Coatings obtained from conventional monomers such as hexanediol diacrylate, trimethylol-propane triacylate or pentaerythritol tri- and tetra-acrylates were much less effective in the protection of organic glasses toward outside solvents. Further, the coatings made according to the invention were generally very hard and effectively protected the organic glasses from scratches resulting from accidental contacts with hard objects. Also, their adhesive power was excellent and they could not be removed from such substrates by usual mechanical means.

Table 3, below, summarizes some results obtained from various Compounds (I), identified again by the nature of their substituents R, R' and A, which were Although the examples have been limited to methylene and ethylene, the propylene and butylene are additional homologs that one skilled in the art would expect to form similar compounds with but only a slight loss in hardness and strength properties.

We claim:

1. A compound having the formula

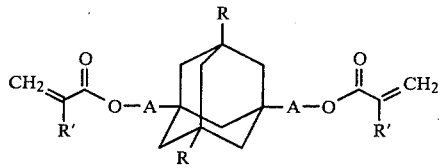

wherein R is a radical selected from the group consisting of hydrogen or methyl; R' is a radical selected from the group consisting of hydrogen or methyl; and A is either a sigma (σ) bond; or a radical satisfying the formula (CH₂)η where η is an integer of from 1 through 4; or phenylene; or an alkyl derivative of phenylene.

2. The compound of claim 1 wherein A is a sigma bond.

3. The compound of claim 1 wherein A is —CH₂—or —CH₂—CH₂—.

4. The compound of claim 1 wherein A is a phenylene group.

5. The compound of claim 2, 3, or 4 wherein R and R' both are hydrogen.

6. The compound of claim 2, 3, or 4 wherein R and R' both are methyl groups.

7. The compound of claim 2, 3, or 4 wherein R is hydrogen and R' is a methyl group.

8. The compound of claim 2, 3, or 4 wherein R is a methyl group and R' is hydrogen.

* * * * *